United States Patent [19]

Edwards et al.

[11] Patent Number: 4,685,902
[45] Date of Patent: Aug. 11, 1987

[54] DISPOSABLE RESERVOIR CASSETTE

[75] Inventors: Floyd V. Edwards, Hopatcong; Hasmukh Shah, East Windsor, both of N.J.

[73] Assignee: Becton, Dickinson and Company, Franklin Lakes, N.J.

[21] Appl. No.: 848,901

[22] Filed: Apr. 4, 1986

Related U.S. Application Data

[63] Continuation of Ser. No. 525,921, Aug. 24, 1983, abandoned.

[51] Int. Cl.4 ............................................. B01D 46/00
[52] U.S. Cl. ..................................... 604/153; 604/151
[58] Field of Search ........................... 604/151-153, 604/120, 122-123, 126, 168, 900, 256, 405, 414

[56] References Cited

U.S. PATENT DOCUMENTS

| | | | |
|---|---|---|---|
| 3,859,998 | 1/1975 | Thomas et al. | 604/900 |
| 4,191,181 | 3/1980 | Franetzki | 128/DIG. 12 |
| 4,193,399 | 3/1980 | Robinson | 604/168 |
| 4,298,358 | 11/1981 | Ruschke | 604/126 |
| 4,380,236 | 4/1983 | Norton | 128/DIG. 12 |
| 4,447,230 | 5/1984 | Gula et al. | 604/126 |
| 4,511,355 | 4/1985 | Franetzki | 128/DIG. 12 |
| 4,601,707 | 7/1986 | Albisser et al. | 604/131 |

FOREIGN PATENT DOCUMENTS

| | | |
|---|---|---|
| 2920975 | 11/1980 | Fed. Rep. of Germany . |
| WO81/01658 | 6/1981 | PCT Int'l Appl. . |
| WO82/03556 | 10/1982 | PCT Int'l Appl. . |
| 1554083 | 10/1979 | United Kingdom . |

Primary Examiner—C. Fred Rosenbaum
Assistant Examiner—Sherri Vinyard
Attorney, Agent, or Firm—John L. Voellmicke

[57] ABSTRACT

A disposable reservoir cassette for use with a roller pump delivery system comprises a flexible reservoir tube, an air-permeable, liquid-impermeable element engaging one end of the reservoir tube, a pierceable delivery septum engaging the other end of the reservoir tube and a rigid housing containing the reservoir tube. The housing includes a backstop which supports the tube in a circular path while allowing access to the septum. The housing is adapted to be secured to the roller pump such that the circular path of the tube is adjacent to the path of a pump roller wherein motion of the pump roller compresses the reservoir tube sufficiently to drive any fluid contained therein in the direction of the delivery septum.

28 Claims, 29 Drawing Figures

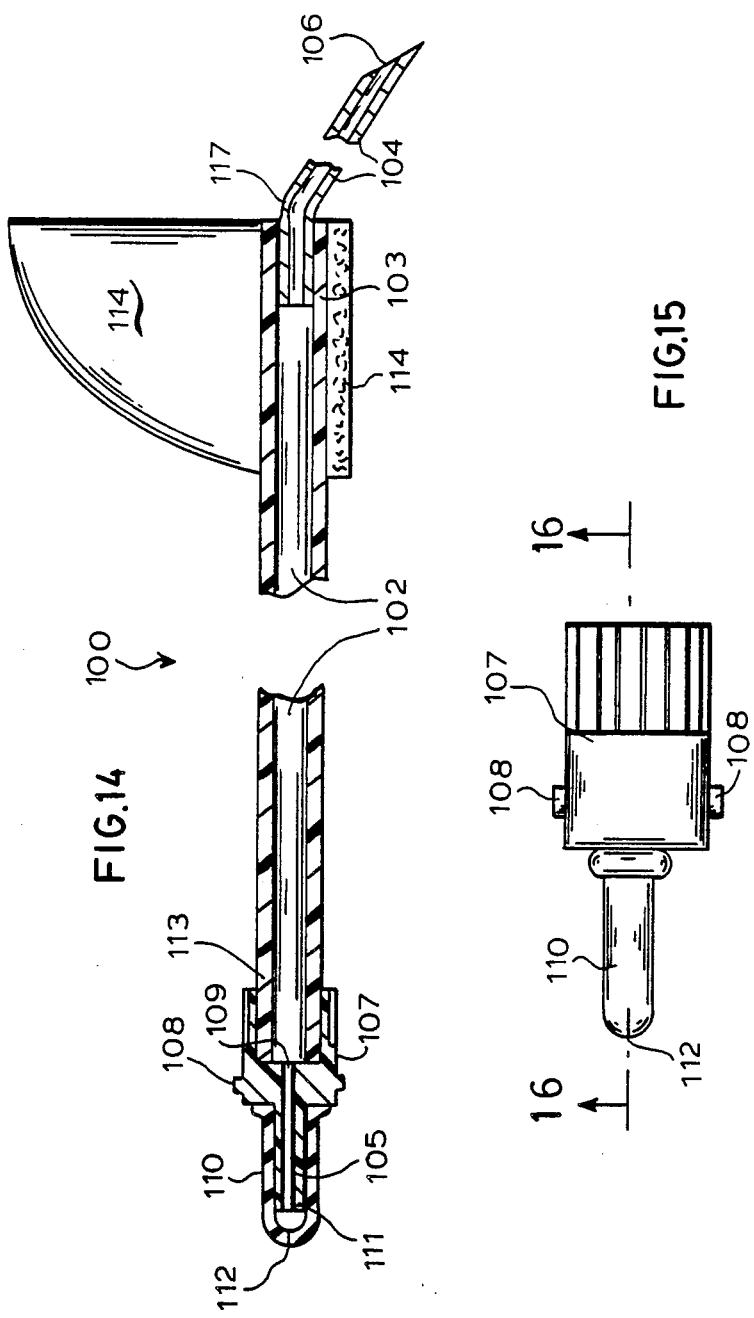

DISPOSABLE RESERVOIR CASSETTE

This application is a continuation of application Ser. No. 525,921, filed Aug. 24, 1983, now abandoned.

FIELD OF THE INVENTION

The present invention relates to a medication delivery system, and more particularly, concerns a disposable reservoir cassette for liquid medication which can be delivered to a patient preferably through the use of a roller type infusion pump, and a reusable injection catheter to contain the liquid medication as it passes from the reservoir cassette to a patient.

DESCRIPTION OF THE PRIOR ART

Many diseases of man and animal are treated by the subcutaneous, intramuscular or intravenous injection of medication into the body of the afflicted being. For example, a common method of treating diabetes mellitus is through the subcutaneous injection of insulin on a daily regimen. This method of treatment fails to entirely normalize glucose metabolism and therefore effects other aspects of metabolism and body chemistry. It is now recognized that relatively large doses of insulin spaced many hours apart can cause microvascular, neuropathic and other complications which may be minimized or eliminated by more frequent smaller subcutaneous doses of insulin. However, more frequency doses present convenience problems for the patient who must continuously carry an ample supply of needles and syringes, and must also remember the exact times for insulin injection and find a private place for administering the injection. In addition, the pain and tissue trauma resulting from frequency injections of small doses of insulin makes this approach impractical. It is more desirable to subcutaneously place an indwelling needle in the patient and intermittently deliver the insulin into the patient's body, or to continuously deliver insulin through an indwelling intramuscular needle or intravenous catheter. However, continuous or intermittent injection over a period of time, for example, twenty-four hours, is impractical without a lightweight compact delivery system which can be attached to the patient's body or clothing while not interfering with his or her daily activities.

Both Muller (U.S. Pat. No. 3,384,080) and Maxwell (U.S. Pat. No. 3,198,385) teach devices capable of continuous injection of fluids into the human body. However, these devices are large and cumbersome and are not readily adaptable to the conveniently attached to the patient's body. Muller requires a separate reservoir which adds to the bulk of the pump unit. Also, a large separate reservoir system presents a potentially life threatening problem in the event that safety devices fail and the pump injects the entire reservoir into the patient. Maxwell teaches a very complex device for high pressure injection in which an ampule is drawn through a pair of rollers, one of which is powered, to squeeze the fluid therefrom.

Xanthopoulos (U.S. Pat. No. 4,187,057) teaches a disposable cassette for use in a peristaltic infusion pump and Brown (U.S. Pat. No. 4,256,437) also is concerned with a peristaltic infusion pump. The Xanthopoulos pump appears large and cumbersome and not suitable for attachment to a patient's body. It is also intended to pump intravenous fluids from a separate reservoir. Xanthopoulos teaches moving the cassette in and out of the operative position, in which pump rollers engage and compress the cassette's first tubular section, by moving the entire cassette in a plane which is parallel to the plane of rotation of the rollers. This type of structure is undesirable in that moving of the cassette in the plane of the roller may cause medication to be injected into the patient as a result of the relative motion between the cassette tube and the rollers.

The patent application of Albisser et al., presently licensed to the assignee hereof, (Ser. No. 267,364 and filed on May 22, 1981) teaches a compact device for controlled subcutaneous injection of medicaments such as insulin in discrete quantities at selected time intervals. Albisser et al. describe a compact roller type pump designed to deliver liquid through a flexible tube connected to a subcutaneously positioned needle. The user of the Albisser et al. invention places the tube needle assembly into the roller pump and then inserts the needle into the insulin vial. The pump is then used to draw insulin from the vial into the tube. The needle is then removed from the vial and placed into the patient. This method requires removing the needle from the patient every time the supply of medication is exhausted.

Also of interest is U.S. Pat. No. 4,235,234 issued to Whitney et al. which teaches a subcutaneous injection system including a locator pad carrying a needle with a right angle bend. The part of the needle before the bend is in the plane of the locator pad and the part after the bend, which includes the sharpened end, projects a prescribed distance, generally perpendicular, from the locating pad. Since the locating pad lies against the patient's skin, the depth of needle penetration is positively controlled.

U.S. Pat. No. 2,847,995 to Adams shows a known spring resilient valve sheath used to seal the end of a needle cannula. This structure is commonly used with evacuated blood collection tubes having a rubber stopper. Pushing the tube stopper toward the end of the cannula will cause the cannula to pierce the sheath and pass through the stopper, thus establishing fluid communication between the interior of the evacuated blood collection tube and the cannula. As the cannula penetrates the rubber stopper, the sheath is compressed in an accordion-like fashion. When the needle is removed from the stopper, the sheath returns to its original position sealing the cannula.

With the above-mentioned deficiencies of the prior art in mind, it is desired to provide a disposable reservoir cassette which can be inserted into and removed from a pump mechanism without removal of the delivery needle from the injection site and to allow the use of the same catheter tubing and delivery needle with consecutively used reservoirs. It is further desired to provide a disposable reservoir cassette which can be purchased by the user in a pre-filled condition or filled by the user with a simple inexpensive filling system. It is still further desired to provide a disposable reservoir cassette which is easy to install and easy to remove from the pump and which will not force additional medication into the patient during the installation and removal procedures and which will also allow the user to conveniently carry and use spare reservoir cassettes.

SUMMARY OF THE INVENTION

The disposable reservoir cassette of the present invention comprises a compressible reservoir, a gas-permeable, liquid-impermeable element at one end of the reservoir and access means at the other end of the reservoir for gaining entry thereinto. A housing means is provided for holding the reservoir so that the access means is accessible for transferring fluid from the reservoir and for allowing contact with the reservoir by externally applied forces adapted to compress the reservoir against the housing means and drive any fluid contained therein in the direction toward the access means.

In a preferred embodiment of this aspect of the invention, a disposable reservoir cassette for use with a roller pump mechanism in delivering liquid medication to a patient comprises a flexible reservoir tube, an air-permeable, liquid-impermeable element at a first end of the tube and a purge chamber connected to the second end of the tube. A purge chamber includes a cylinder, a pierceable septum at one end of the cylinder and a sealing member at the other end of the cylinder. The septum, cylinder and sealing member define a cavity for accepting and storing a portion of the fluid originally contained within the tube. The sealing member contains a centrally located orifice which is in fluid communication with the second end of the tube. Air venting means between the interior of the purge chamber and the exterior of the purge chamber is provided to allow gases to escape the purge chamber when fluid enters same. Also provided is a rigid cassette housing containing the reservoir tube therein. This housing includes an opening to accept an externally positioned roller of the roller pump mechanism and a rigid substantially circular backstop supporting the tube along the length of the tube. The housing has a transfer port therein and means to fixedly hold the tube adjacent to the backstop so that the second end of the tube is adjacent to the transfer port. Securement means is provided for cooperating with the roller pump to position and removably hold the housing so that the backstop is located substantially adjacent to the path of the roller pump roller whereby rotation of the roller compresses the tube sufficiently to drive any fluid contained therein in the direction toward the second end of the tube.

In another aspect of the present invention, a reusable injection catheter comprises a flexible conduit, injection means associated with the first end of the conduit for delivering medication into a patient and a cannula extending outwardly from a second end of the conduit with a free end of the cannula being furthermost from the conduit. Sealing means is associated with the cannula for normally preventing the passage of fluid therethrough. This sealing means is responsive to externally applied force or fluid pressure for allowing fluid passage through the cannula.

In a preferred embodiment of this other aspect of the invention, a reusable injection catheter for use with a source of externally supplied pressurized fluid comprises a flexible tube, a first cannula extending outwardly from a distal end of the tube adapted for insertion into a patient and a connector housing at a proximal end of the tube. This housing has a forward end, a rearward end adjacent to the tube and a passageway therethrough. The passageway is in fluid communication with the tube. A second cannula extends outwardly from the forward end of the housing passageway. A free end of the second cannula is furthermost from the housing. Also provided is a resilient sleeve covering the free end of the second cannula to prevent fluid passage therethrough. This sleeve includes a closed end adapted to be pierced by the free end of the second cannula upon the application of an external force to the sleeve in a direction along the second cannula toward the housing thus allowing fluid passage through the second cannula. The sleeve is further adapted to return to its original position upon termination of the external force. Attachment means associated with the housing cooperates with the source of externally supplied pressurized fluid to removably hold the housing in a fixed position relative thereto. In this fashion the second cannula and the sleeve are held in a position with the closed end of the sleeve being pierced by the second cannula whereby the second cannula is free to accept fluid through its free end.

In accordance with the principles of the present invention, a number of advantages and objectives are achieved. Primarily, the present invention provides a disposable reservoir cassette and a reusable injection catheter for use in a compact medication delivery system for injecting continuous or incremental doses of liquid medication into a patient. The present invention is particularly adapted for utilization with a programmable body-attachable roller pump. The present invention provides a disposable reservoir cassette which can be purchased by the user in a pre-filled condition or filled by the user with a simple inexpensive filling device. This reservoir cassette is easy to install and easy to remove from the roller pump and will allow the user to conveniently carry and use spare reservoir cassettes. In addition, the reservoir cassette can be inserted and removed from the roller pump without removal of the delivery needle from the injection site and, as a result of the purge chamber, it allows the use of the same catheter tubing and delivery needle for consecutively used reservoirs. The reusable injection catheter assists in this respect by providing a resilient sleeve or sealing means which prevents medication from leaving the catheter during a change of reservoirs. Further, containment of all of the medication within the cassette avoids the problems associated with delivering medication from a large adjacent reservoir.

BRIEF DESCRIPTION OF THE DRAWINGS

FIG. 14 is an enlarged partial cross-sectional view, looking along the longitudinal axis, of the reusable injection catheter of FIG. 13;

FIG. 15 is an enlarged side elevation view of the connector housing with resilient sleeve of the preferred reusable injection catheter;

DETAILED DESCRIPTION

Figure 1:
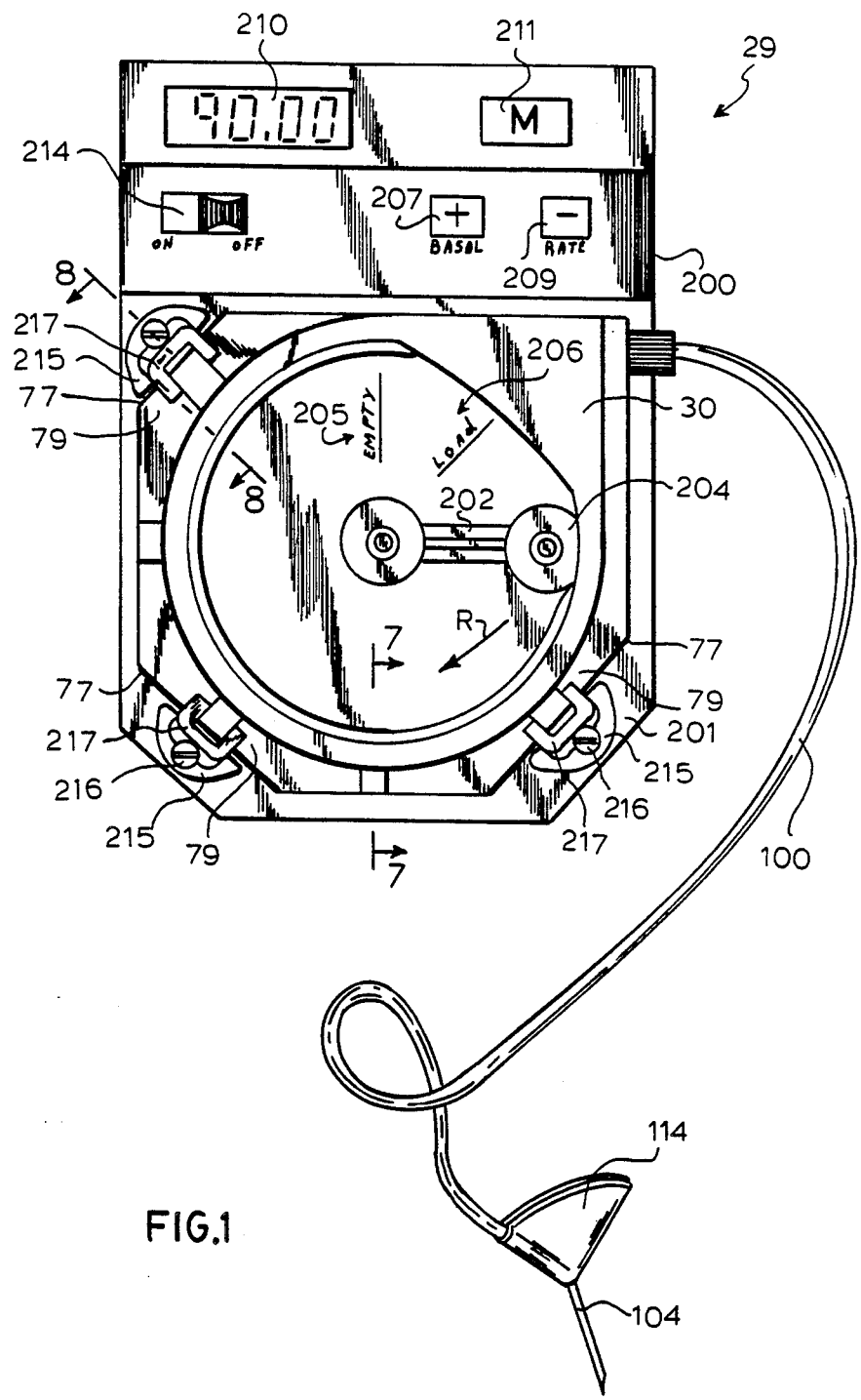
FIG. 1 is a top plan view of the preferred disposable reservoir cassette attached to a programmable roller pump with the preferred reusable injection catheter attached to the reservoir cassette.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Turning to FIG. 1, an operable medication delivery system 29 for the delivery of liquid medication, such as insulin, to a user includes a disposable reservoir cassette 30, a programmable electrically contolled roller pump 200 and a reusable injection catheter 100. The roller pump is preferably a reusable electro-mechanical miniature roller pump adapted to be attached to the human body and similar to the pump described in the above mentioned application of Albisser et al. The principle of operation of the delivery system is based upon a peristaltic motion modified to deliver the entire contents of disposable reservoir cassette 30 in the single pass of a roller. As will hereinafter be described, the contents of the reservoir cassette are delivered through the injection catheter and into the patient.

The roller pump of the embodiment being described includes a rigid dust proof water resistant body housing 201 which contains a drive mechanism, an electronic package and a power source, all of which are not shown. Projecting outwardly from housing 201 is roller driving arm 202 and a pump roller 204. The drive mechanism which drives roller 204, through arm 202, is an internal spring (not shown) which is rewound each time the pump is loaded with a new reservoir cassette. The winding is performed when the roller driving arm is manually rotated in a counter-clockwise direction from an empty position 205 to a load positio 206. An internal indexing mechanism (not shown) contrains the clockwise roller movement to discrete angular increments of 1.5 degrees and is activated by the electronic package. The electronic package times and activates the indexing mechanism and is adjustable to provide automatic roller movement from one increment every 88.2 minutes to one increment every fifteen minutes. The rate of roller incremental movement is proportional to the basal rate which is the rate insulin is delivered from the delivery system. Adjustments can be made in the basal rate, for example, so that U-100 insulin is delivered from 0.34 units per hour to 2.00 units per hour. The basal rate is adjusted up or down by activating buttons 207 or 209 on the housing and observing the rate in a liquid crystal display 210. A bolus button 211 is provided to permit manual control of roller incrementation and to allow delivery of insulin in amounts greater than the basal rate. This feature allows the user to receive additional insulin when needed, for example, before meals. On/off switch 24 is provided to control that part of the electronic package which supplies power to the internal indexing mechanism, thereby acting as a control to start and stop the incremental movement of the pump roller.

Figure 2:
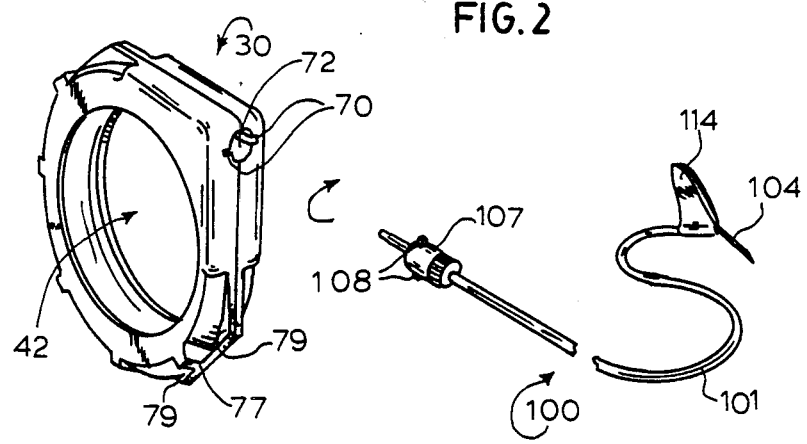
FIG. 2 is a perspective view of the preferred disposable reservoir cassette and the preferred reusable injection catheter.
Figure 3:
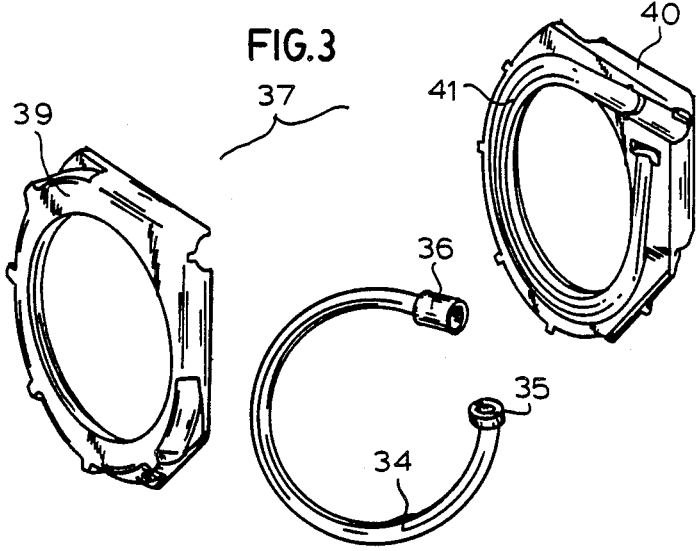
FIG. 3 is exploded perspective view of the preferred disposable reservoir cassette.
Figure 4:
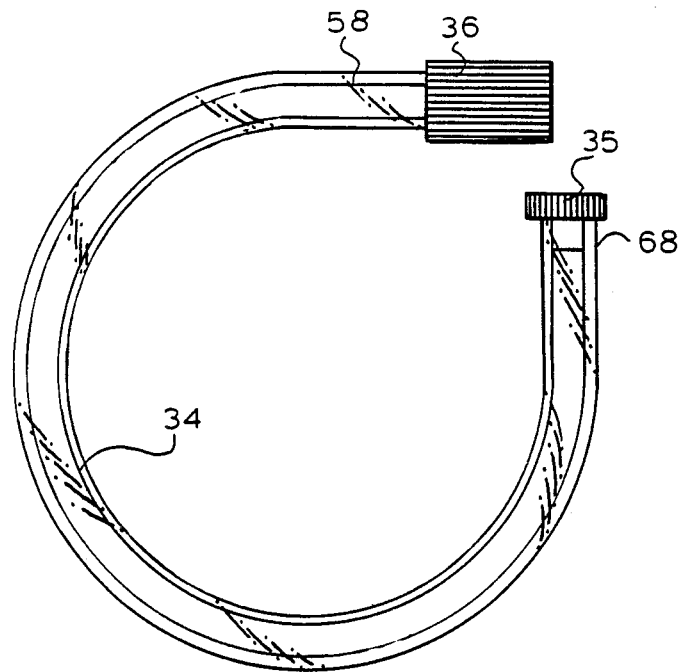
FIG. 4 is an enlarged top plan view of the reservoir tube, as part of the reservoir cassette with purge chamber and the air-permeable, liquid-impermeable element.

Turning to FIGS. 2-4 disposable reservoir cassette 30 includes a flexible reservoir tube 34, an air-permeable, liquid-impermeable element 35 at a first end 68 of the reservoir tube and a purge chamber 36 at a second end 58 of the reservoir tube. The reservoir tube is shapable along its length so as to take on a circular, ring-shaped configuration. A rigid cassette housing 37 contains the reservoir tube, the purge chamber and the element. The housing includes a rigid substantially circular backstop 41 which supports the reservoir tube along the length of the tube, an opening 42 to accept the roller pump roller and a transfer port 72 adjacent to the purge chamber. Cassette housing 37 includes an upper housing portion 39 and a lower hosing portion 40.

Figure 5:
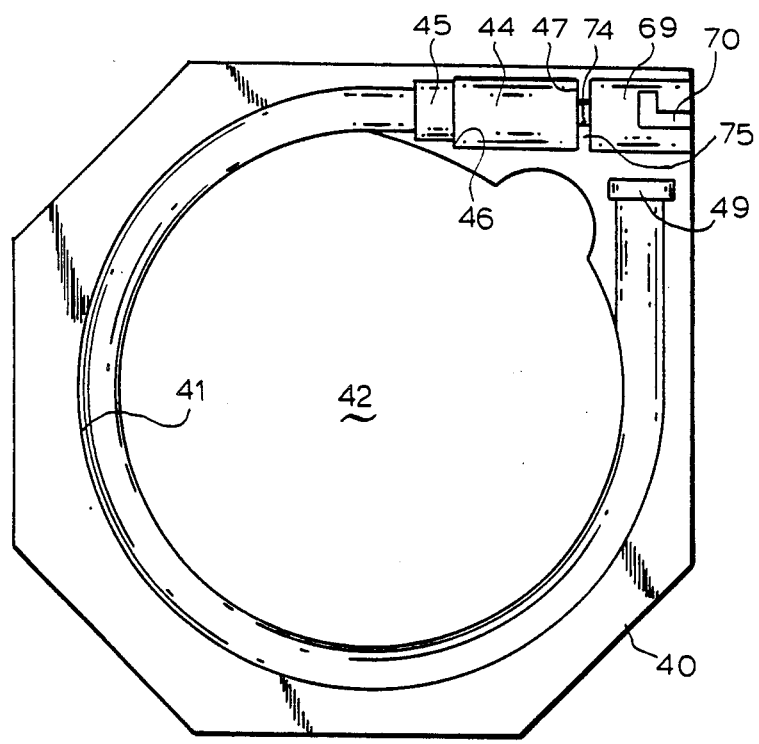
FIG. 5 is an enlarged top plan view of the lower housing portion of the reservoir cassette.
Figure 6:
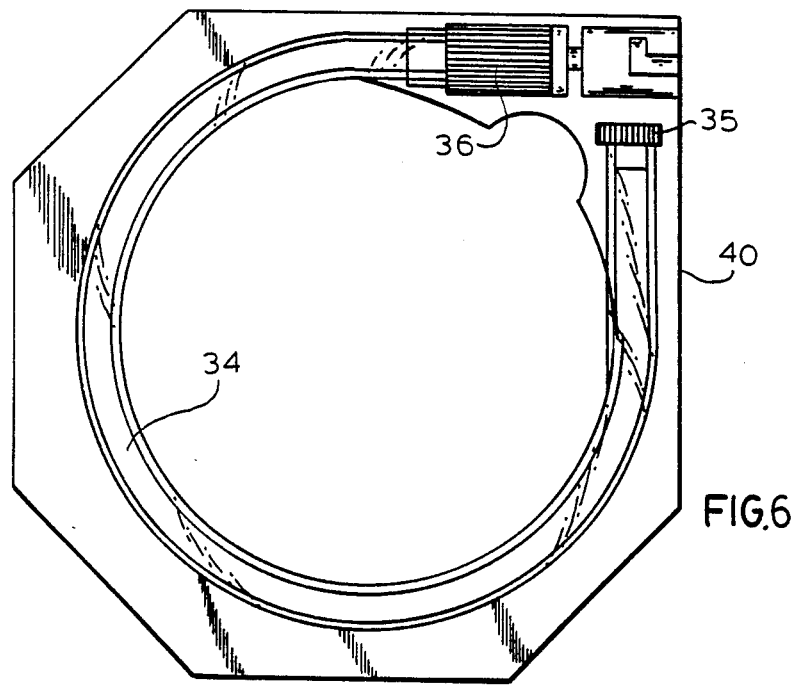
FIG. 6 is an enlarged top plan view of the reservoir tube with purge chamber and air-permeable, liquid-impermeable element in the lower housing portion of the reservoir cassette.
Figure 7:
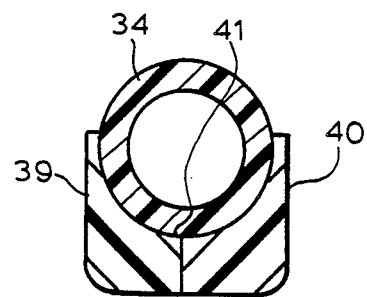
FIG. 7 is an enlarged cross-sectional view of the disposable reservoir cassette of FIG. 1 taken along line 7—7.

As seen in FIGS. 5-7, lower housing portion 40 includes a circular purge chamber recess 44, a circular reservoir tube recess 45, a shoulder 46 between recess 44 and recess 45 and a purge chamber shoulder 47 at the end of purge chamber recess 44 opposite shoulder 46. Also included in lower housing portion 40 is circular transfer port recess 69, one of two connector housing retaining grooves 70, sleeve retaining wall 75 and circular cannula conduit recess 74. When the reservoir tube with purge chamber and element attached is placed in lower housing portion 40, as shown in FIG. 6, purge chamber 36 is received in recess 44 between shoulders 46 and 47. Likewise, element 35 at the opposite end of the reservoir tube is received in an element recess 49 in the lower housing portion. Upper housing portion 39 contains similar recesses, grooves and shoulders so that when the upper housing and lower housing are joined, the purge chamber and element are enclosed therein. As a result of this structure, the longitudinal motion of the reservoir tube is limited to thereby reduce dosage inaccuracies that may result from the reservoir tube moving along the backstop in response to roller motion. A similar result can be achieved by using adhesive to attach the reservoir tube along the length of the backstop or by providing cooperating structure along the tube and along the backstop to maintain the relative position of the tube with respect to the backstop. It will be apparent to one skilled in the art that numerous constructions could be used to contain the reservoir tube within the housing portions and that the arrangements described above are exemplary of these many possibilities. The joining of the upper and lower housing portions also causes the formation of transfer port 72 and a circular cannula conduit which includes cannula conduit recess 74 and a similar recess in housing portion 39. The cannula conduit connects the purge chamber recess and the transfer port.

In the preferred embodiment of the present invention, the housing portions are made of thermoplastic material which can be joined together via cooperating structure in the housing portions, fasteners, adhesive or the use of compatible welding techniques. The preferred disposable reservoir cassette is a compact structure measuring approximately 2.0 inches (5.08 cm) wide by 2.0 inches (5.08 cm) high by 0.3 inch (0.76 cm) thick. It is also within the purview of this invention to include housing portions which are removably attached to each other so that the housing portions are reusable while the reservoir tube, with purge chamber and element attached, is disposable after one use. Housing portions may be made to removably attach to each other by using threaded screw type fasteners, snap fasteners or other suitable reusable connecting means to hold the housing portions together.

Figure 8:
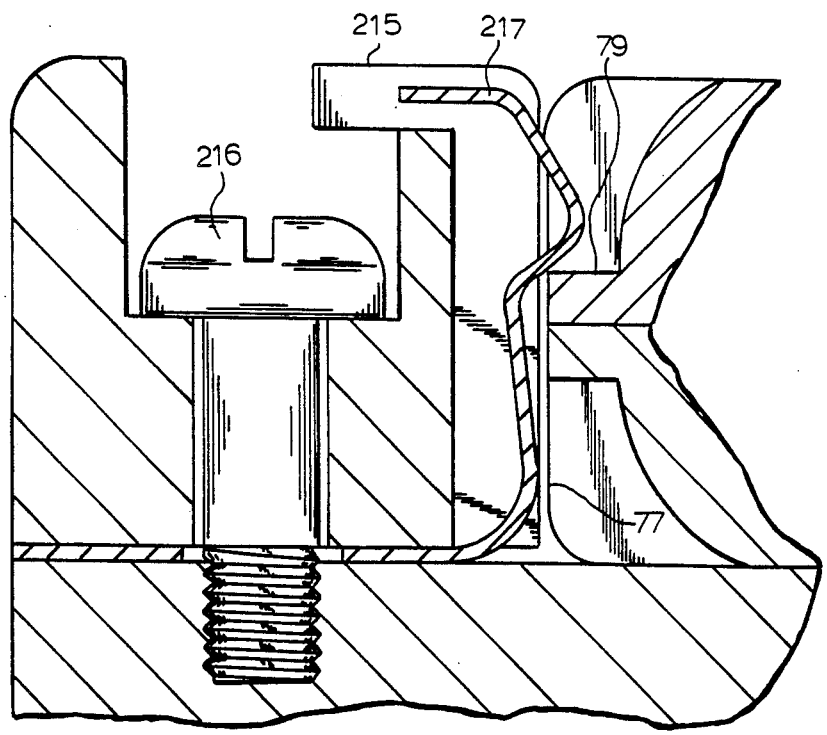
FIG. 8 is an enlarged partial cross-sectional view of the preferred disposable reservoir cassette and the roller pump of claim 1 taken along line 8—8.

Averting to FIGS. 1 and 8, disposable reservoir cassette 30 must be held in a removably fixed relationship to roller pump 200 and in particular to the path of pump roller 204. Since medication is delivered to the patient through the action of the pump roller as it moves along a circular path compressing flexible reservoir tube 34, it is important that the reservoir cassette be restrained from rotational movement with respect to the roller pump. If the cassette rotates in the direction of roller motion, less medication will be delivered than is required while rotational motion of the cassette in the direction opposite of roller motion will cause more medication to be delivered than is required. Also, as will become apparent, it is important that the reservoir cassette be installed and removed without rotational movement with respect to the roller pump so that medication is not delivered or air drawn into the system during the removal and installation procedure.

To prevent rotational motion of disposable reservoir cassette 30 with respect to roller pump 200, positioning surfaces 77 are provided on cassette housing 37. These positioning surfaces are adjacent to positioning blocks 215 which are attached to the roller pump housing via positioning screws 216. Positioning blocks 215 can be adjusted to be in close proximity to cassette housing positioning surfaces 77 and then fixed in that position by tightening screws 216. It can be seen that rotational motion of the disposable reservoir cassette with respect to the roller pump can be substantially restrained through this structure. It should be noted that close control of the dimensional tolerances of the various positioing surfaces should allow positioning blocks to be made without adjusting screws and as an integral part of the roller pump housing. The above described cooperating surfaces also restrict the motion of the disposable reservoir cassette with respect to the roller pump so that the disposable reservoir cassette must be moved in a direction substantially perpendicular to the path of the pump roller when it is being attached to and removed from the roller pump, thus minimizing the chance of accidental medication delivery or drawing air into the system.

Retention springs 217 apply pressure to cassette housing outwardly extending exterior longitudinal ribs 79 to hold the reservoir cassette against the roller pump housing. The retention springs can be deflected out of the way by forced movement of the reservoir cassette in a direction perpendicular to pump roller motion, thus providing a snap-fit arrangement to hold the reservoir cassette in a removable fixed relationship with the roller pump. Retention springs 217 are held in in place by retention screws 216.

Figure 9:
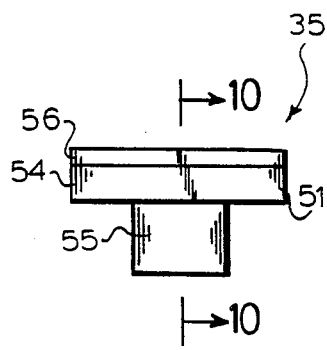
FIG. 9 is an enlarged side elevation view of the air-permeable, liquid-impermeable element of the preferred disposable reservoir cassette.
Figure 10:
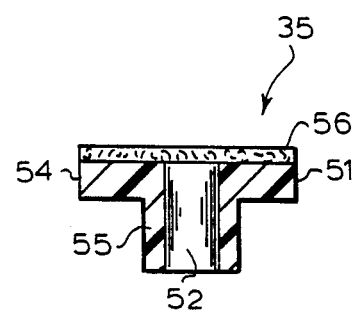
FIG. 10 is a cross-sectional view of the element of FIG. 9 taken along line 10—10.

FIGS. 9 and 10 depict a preferred air-permeable, liquid-impermeable element 35 which includes a plug 51 with a passageway 52 therethrough. The plug includes a flanged portion 54 which is larger in diameter than the outside diameter of the reservoir tube and a body portion 55 which is inserted in the reservoir tube. The plug may be held in the reservoir tube through the use of an interference fit wherein the outside diameter of body portion 55 is slightly larger than the inside diameter of the tube or by the use of adhesives or the like. Air-permeable, liquid-impermeable membrane 56 is attached to the plug so that passageway 52 is covered. With this construction, gases entering or leaving the plug end of the reservoir tube must pass through the membrane while the liquid medication contained within the reservoir cannot pass therethrough. In some cases, as will later be shown, it may be desirable to use a porous membrane with a maximum pore rating of about 0.5 microns for filtering particulate matter including microorganisms from gas entering into the reservoir tube. The membrane may be attached to plug 51 via the use of adhesives or heat sealing. It is also within the purview of this invention to include a plug made entirely of air-permeable, liquid-impermeable material thereby eliminating the need for a passageway and a separate membrane.

Figure 11:
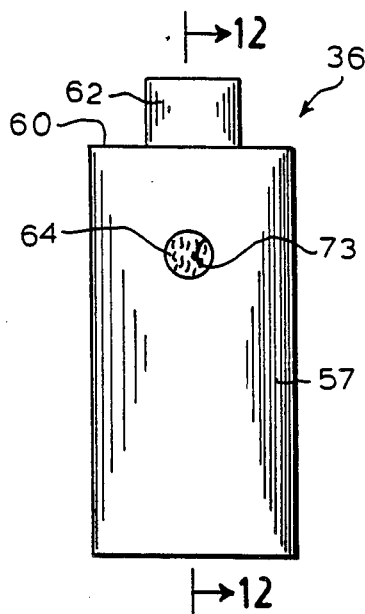
FIG. 11 is an enlarged side elevation view of the purge chamber of the preferred disposable reservoir cassette.
Figure 12:
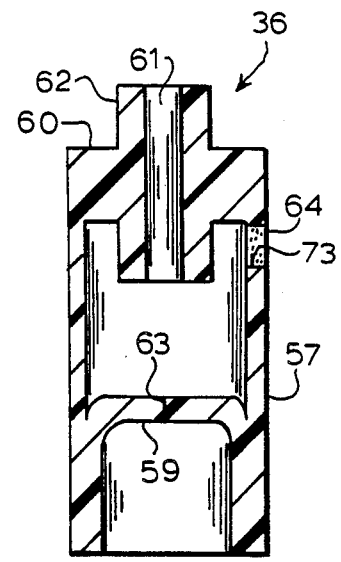
FIG. 12 is a cross-sectional view of the purge chamber of FIG. 11 taken along line 12—12.
Figure 13:
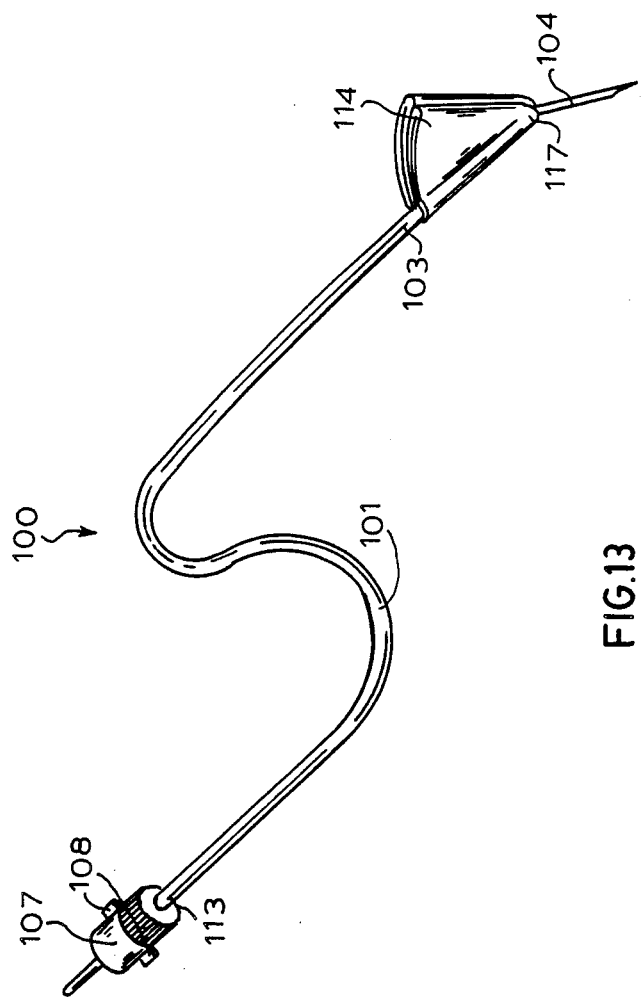
FIG. 13 is a perspective view of the preferred reusable injection catheter.
Figure 16:
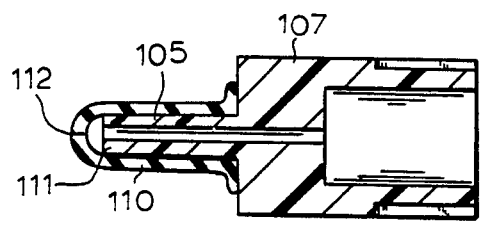
FIG. 16 is a cross-sectional view of the connector housing of FIG. 15 taken along line 16—16.
Figure 17:
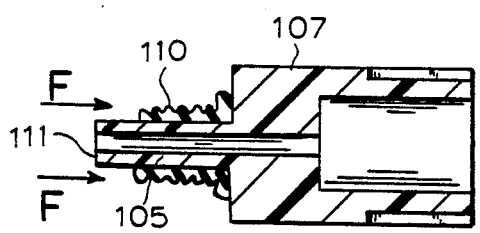
FIG. 17 is the connector housing of FIG. 16 further showing the second cannula projecting through the slit in the resilient sleeve.

Adverting to FIGS. 11 and 12, there is illustrated preferred purge chamber 36 which includes a cylinder 57, a pierceable septum 59 located at one end of the cylinder and a sealing member 60 located at the other end of the cylinder. The cylinder and the sealing member may be made of rigid materials or resilient elastomeric materials, with the latter being preferred. Pierceable septum 59 is preferably made of resilient elastomeric material with a normally closed slit 63 centrally located therein. Slit 63 is forced open by components, hereinafter described in more detail, when medication is being placed into or forced out of the reservoir tube. In addition to the slit, it is within the purview of this invention to include other self-sealing structures such as a solid elastomeric septum, a duck-bill or miter valve, or the like, as part of the pierceable septum, with the slit structure being exemplary of the many possible variations. Adhesive may be used to attach pierceable septum 59 to cylinder 57. The sealing member includes a centrally located orifice 61 which is in fluid communication with second end 58 of reservoir tube 34. Reduced diameter portion 62 of the sealing member is inserted into the second end of the reservoir tube. An interference fit wherein the outside diameter of reduced diameter portion 62 is larger than the inside diameter of the reservoir tube may be used to join these parts. Adhesive or other suitable means may also be used to join the purge chamber and the reservoir tube. A purge chamber port 73 contains an air-permeable, liquid-impermeable filter 64 which communicates between the interior of the purge chamber and the exterior thereof so that gases which may be contained in the purge chamber may exit when medication enters the purge chamber. Filter 64 may be in the form of an element attached within port 73 in cylinder 57 or in the form of a sheet attached so that it covers port 73 in cylinder 57.

Turning now to FIGS. 13–17, preferred reusable injection catheter 100 includes a flexible conduit 101 having a lumen 102 therethrough and a first cannula 104 at distal end 103 of the flexible conduit in fluid communication with the conduit. The first cannula has a sharpened beveled point 106 for easy insertion into the patient. Adhesive is preferably used to hold the first cannula in the flexible conduit. It is preferred that the first cannula include a bent section 117 in an area adjacent to the distal end of the flexible conduit. The bent portion should cause the free end of the first cannula to project outwardly from flexible conduit 101 at an obtuse angle relative to the longitudinal axis of an within the flexible conduit. It is preferred, but not necessary, that this obtuse angle be within the range of about 120 to 160 degrees. The length of the flexible conduit depends on the distance between the roller pump and the injection site. It is preferred that the inside diameter of flexible conduit 101 be about 0.43 mm (0.017 inches).

A connector housing 107, having a passageway 109 therethrough is provided at proximal end 113 of conduit 101. Preferably, the connector housing is made of a thermoplastic material and is attached to the flexible conduit via the use of adhesive or other suitable means. Connector housing projections 108 extend radially outwardly from the surface of connector housing 107 and are sized and positioned to engage connector housing retaining grooves 70 of cassette housing 37. A second cannula 105 extends outwardly from the connector housing and is in fluid communication with passageway 109. The second cannula may be an integral part of the connector housing or a separate cannula attached to the housing. As will be shown, it is not necessary for the second cannula to have a sharpened point. A resilient sleeve 110 covers a free end 111 of the second cannula to prevent fluid passage therethrough. This sleeve is made of elastomeric material with a normally closed slit 112 at the closed end thereof. As will be explained in more detail hereinafter, the application of an external Force F to resilient sleeve 110 in the direction of connector housing 107 causes the sleeve to collapse in an accordion-like fashion and allow second cannula to pass through slit 112 thus allowing fluid to flow into the second cannula. Withdrawal of the external force allows the resilient sleeve to return to its original position in which it prevents fluid flow through the second cannula and therefore prevents any liquid medication which may be in the flexible conduit from exiting through the second cannula.

It is also within the purview of the present invention to include a one-way valve means in the connector housing passageway to prevent fluid from leaving the flexible conduit through the second cannula while force or fluid pressure in a direction into the second cannula toward the flexible conduit opens the valve means and allows fluid flow therethrough.

Figure 18:
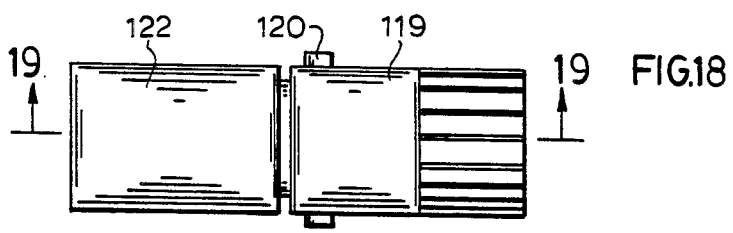
FIG. 18 is an enlarged side elevation view of the connector housing and cover member of an alternative embodiment of the reusable injection catheter.
Figure 19:
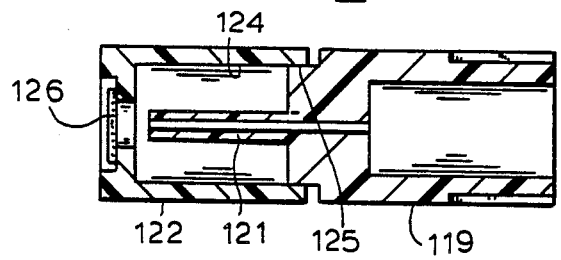
FIG. 19 is a cross-sectional view of the connector housing and cover member of claim 18 taken along line 19—19.
Figure 20:
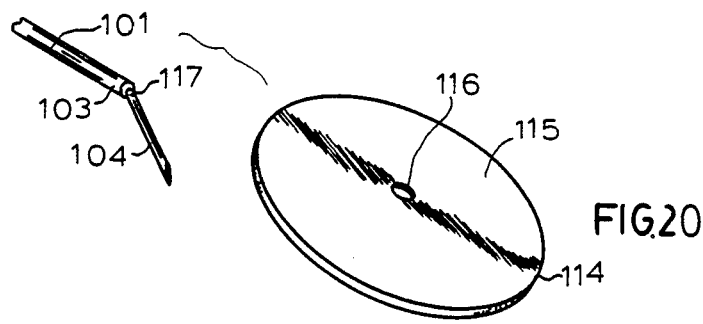
FIG. 20 is a perspective view showing the hold-down member open for assembly to the first cannula end of the preferred injection catheter.
Figure 21:
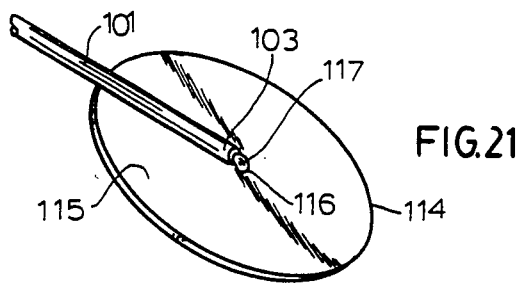
FIG. 21 is a perspective view showing first cannula end of the preferred injection catheter with first cannula inserted into the hold-down member.

As best shown in FIGS. 18 and 19, an alternative embodiment of the reusable injection catheter includes a connector housing 119 and connector housing projections 120 which are sized and positioned to engage connector housing retaining grooves 70. A second cannula 121 extends outwardly from the connector housing. A shield member 122 removably engages the connector housing through an interference fit between shield member inside diameter 124 and a shield member engaging surface 125 on the housing. Shield member 122 is provided to protect second cannula 121 from damage and contamination when connector housing 119 is not engaging the disposable reservoir cassette. Also provided is venting member 126 which allows air trapped within the shield member to escape while the shield member is being engaged with the connector housing. Without venting member 126 the engagement of the shield member and the connector housing could force air into the flexible conduit through second cannula 121. This is undesirable since air in the flexible conduit can be injected into the patient. It is desirable to construct venting member 126 of a filter material which will prevent bacteria from passing therethrough so that second cannula 121, if initially sterile, will not be contaminated during subsequent handling before the shield member is removed. One skilled in the art will recognize that there are numberous ways to design a cover member to engage a housing, e.g. screw fitting and snap-fit, and that there are numerous ways to provide for venting in a cover member and that the above described configuration is exemplary of these many possible configurations.

Figure 22:
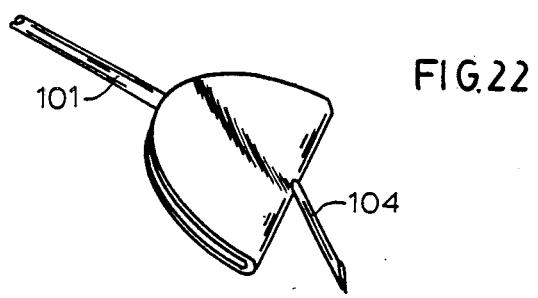
FIG. 22 is the assembly of FIG. 21 with hold-down member folded on an axis perpendicular to the flexible conduit.
Figure 23:
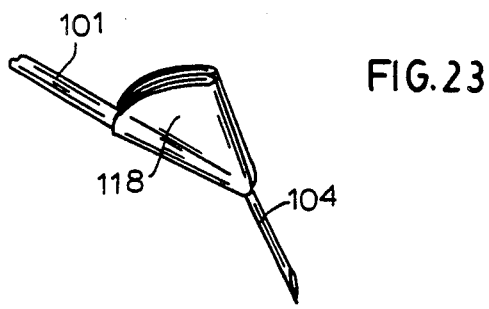
FIG. 23 is the assembly of FIG. 22 with the hold-down member further folded in a position for cannula insertion into the patient.
Figure 24:
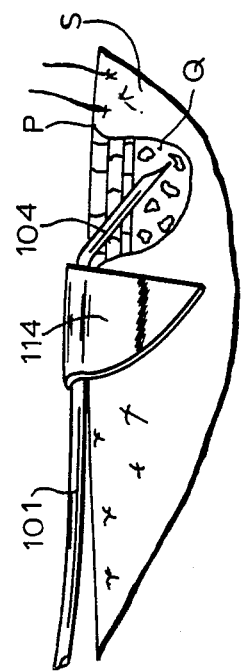
FIG. 24 is an enlarged side elevation view of the distal end of the preferred injection catheter in use.

Referring now to FIGS. 20–24, a hold-down member 114 is provided for securing first cannula 104 to patient P after it has been inserted into the subcutaneous fat layer Q below patient's skin S. The hold-down member may be a circular flexible pad with a first side 115 coated with a contact adhesive. After the first cannula is placed through a centrally located hole 116, member 114 is folded over on itself on an axis which is transverse to flexible conduit 101. The contact adhesive causes member 114 to stay in this folded condition, as best shown in FIG. 22. Member 114 may now be folded again along an axis substantially parallel to flexible conduit 101. In this position, as shown in FIG. 23, the patient may grasp the hold-down member and use it as a handle to assist in the subcutaneous placement of the first cannula. After the cannula is properly placed, the patient releases his grip on member 114 and it returns to the shape shown in FIG. 22 so that it can be taped to the patient's body. The bend in first cannula 104 facilitates the subcutaneous placement of the first cannula. As best shown in FIG. 24 the bend also demands that the needle be lifted away from the skin when being removed, a motion that is constrained by the hold-down member while it is attached to the patient. It is desirable to coat surface 118, which faces the patient, with an adhesive that causes it to removably adhere to the skin and to further cover this adhesive with a backing paper (not shown). Once the needle is properly placed, the patient may remove the backing paper and press surface 118 against skin S, causing the hold-down member to remain removably attached to the skin. It is also within the purview of the present invention to include a hold-down member without a hole for accepting the first cannula wherein the distal end of the flexible conduit is attached to the hold-down member rather than being contained between its layers.

Figure 25:
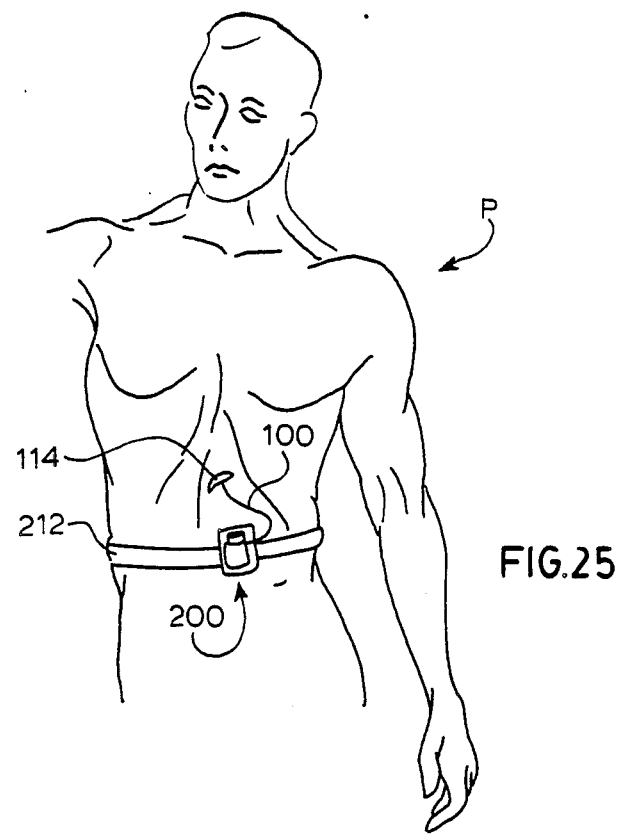
FIG. 25 is a perspective view showing the medication delivery system attached to one desirable position on a patient's body.

Referring to FIG. 25, programmable roller pump 200 may be secured to the patient's body via flexible waist band 212. Since there are a wide variety of possible roller pump locations on the patient or within adjacent garments, the waist mounting illustrated is intended to be exemplary of these many possible positions. Once a location for the programmable roller pump is chosen, the injection site may be any convenient portion on the patient's body which is near to the pump and also contains enough fatty tissue to assure the proper subcutaneous placement of first cannula 104 of the injection catheter, using hold down member 114.

Figure 26:
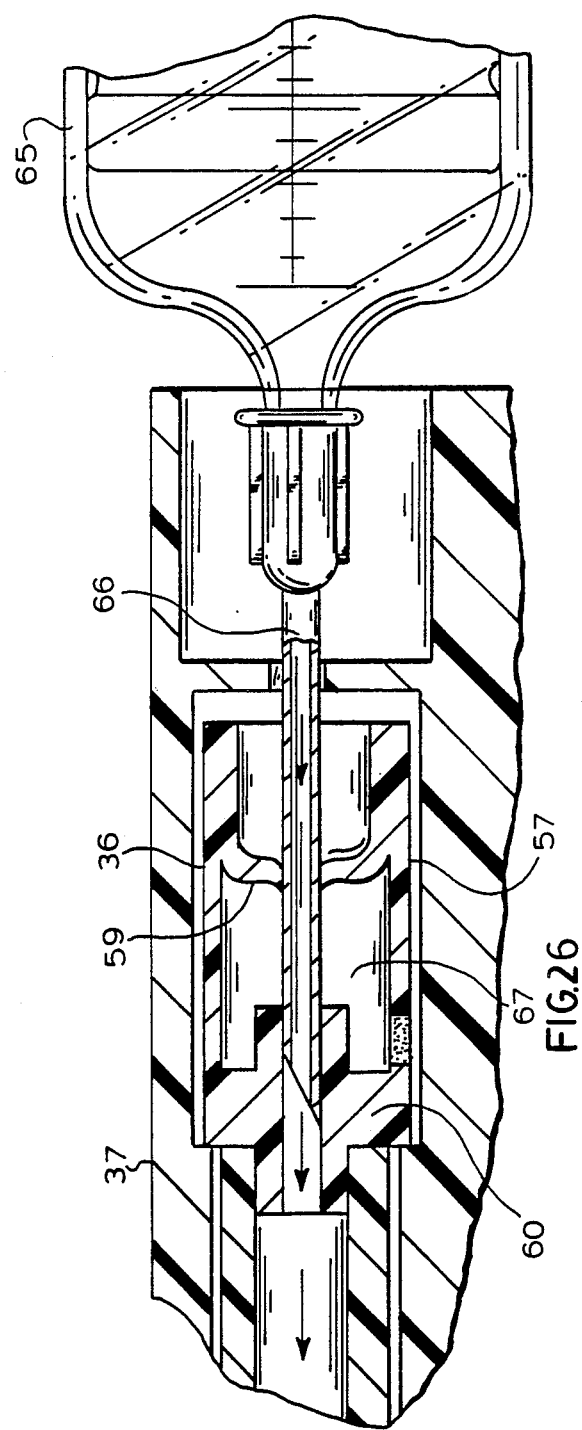
FIG. 26 is an enlarged partial cross-sectional view showing a syringe being used for filling the preferred disposable reservoir cassette.

Averting to FIG. 26, to fill the preferred disposable reservoir cassette (if not prefilled), the user first transfers liquid medication from a standard medication vial, containing a needle-penetrable closure (not shown), to a hypodermic syringe 65 with needle cannula 66 attached thereon. The needle cannula is then pushed through pierceable septum 59 and into sealing member 60 of the purge chamber. The medication is then expelled from the syringe into the reservoir tube. Gases in the reservoir tube which are displaced by the medication exit through element 35, while liquid medication cannot pass therethrough. If an air bubble becomes trapped within the medication in the reservoir tube, it may be eliminated by withdrawing some of the medication back into the syringe along with the air bubble and then manipulating the syringe so that the medication can be returned to the reservoir tube without the air bubble. It can be seen that air drawn into the reservoir tube may contain bacteria. This may not present a problem if the medication contains a bacteristatic agent. However, bacteria can be prevented from passing through the element if it is constructed of material having a maximum pore rating of about 0.5 micron so that the element is capable of filtering microorganisms from the gas entering the reservoir tube. It should be noted that cannula 66 prevents medication from entering interior portion 67 of the purge chamber.

Figure 29:
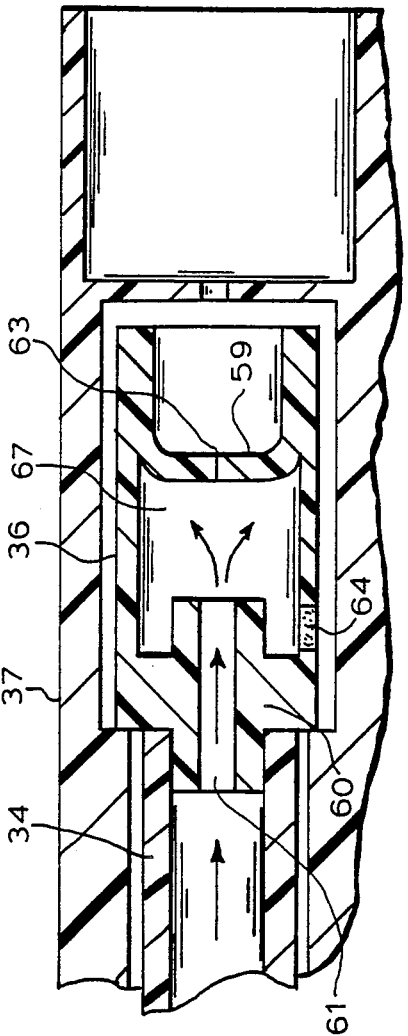
FIG. 29 is an enlarged partial cross-sectional view of the preferred disposable reservoir cassette schematically showing medication entering the purge chamber.
Figure 27:
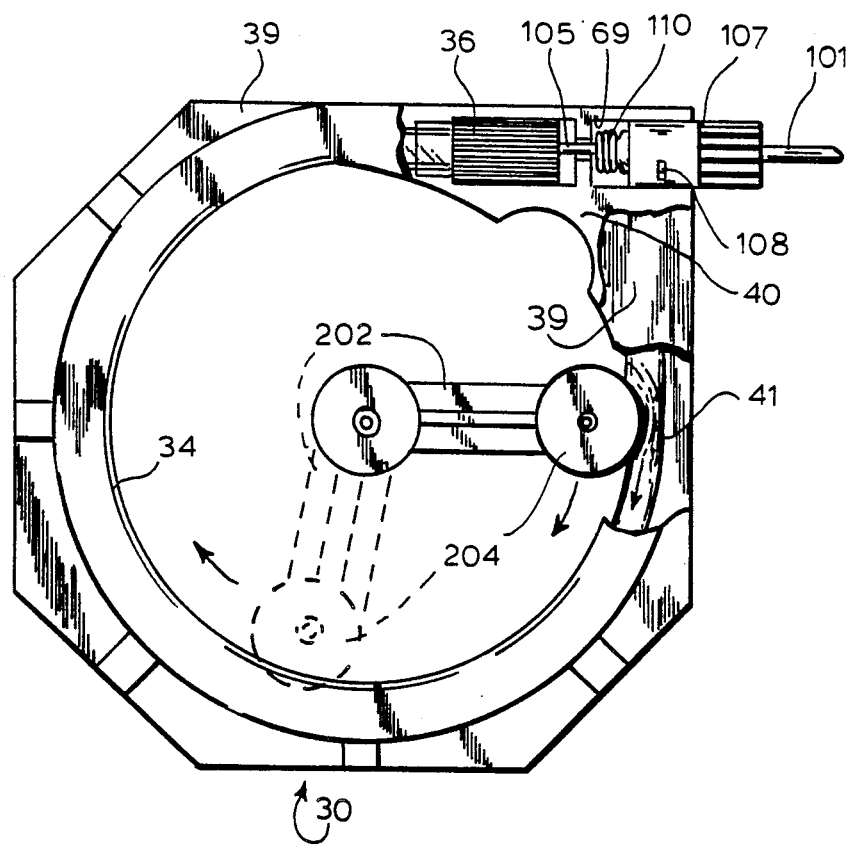
FIG. 27 is an enlarged top plan view of the preferred disposable reservoir cassette partially cut away to show interaction with the preferred reusable injection catheter and the roller pump.
Figure 28:
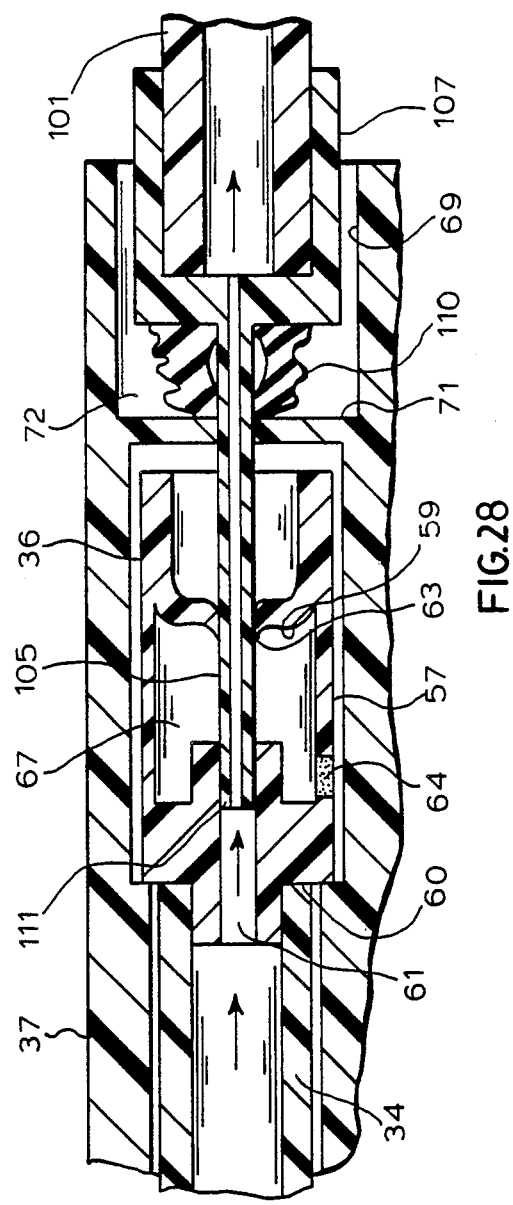
FIG. 28 is an enlarged partial cross-sectional view showing the preferred reusable injection catheter connected to and in fluid communication with the preferred disposable reservoir cassette.

In use, as best shown in FIGS. 27, 28 and 29 together with FIGS. 1 and 8, the patient, with the programmable roller pump attached to his body, rotates roller driving arm 202 in a counter-clockwise direction to the load positio and inserts a disposable reservoir cassette, filled with liquid medication, into the roller pump by placing the reservoir cassette between positioing blocks 215 of the roller pump housing and forcing it directly toward the roller pump to cause retention springs 217 on the pump housing to engage the external ribs on the reservoir cassette housing. Reusable injection catheter 100 is then connected to the reservoir cassette by inserting connector housing 107 into transfer port 72 in the cassette housing so that connector housing projections 108 are aligned with connector housing retaining grooves 70 in the cassette housing. The connector housing retaining grooves will only allow the connector housing to enter the transfer port to a depth which places second cannula 105 in fluid communication with reservoir tube 34, which is filled with medication. At this point, twisting the connector housing locks it into the reservoir cassette in a bayonet fashion. It should be noted that during insertion sleeve shoulder 71 in cassette housing 37 forces resilient sleeve 110 toward the connector housing allowing the second cannula to pierce slit 112 in the resilient sleeve and to thereby open the second cannula for accepting medication from the cassette reservoir. Also, during insertion, exposed free end 111 of second cannula 105 pierces slit 63 in pierceable septum 59 and enters orifice 61 of sealing member 60 such that the second cannula is now in fluid communication with flexible reservoir tube 34.

Pump roller 204 is now advanced to the start position, as best seen in FIG. 1, by depressing and holding bolus button 211. Advancing the pump roller to the start position causes the roller to compress flexible reservoir tube 34 and force a portion of the medication contained therein into the injection catheter simultaneously filling it with medication and forcing all air out of the the fluid path. First cannula 104 may now be inserted subcutaneously into the patient and attached to the patient using hold-down member 114, as previously described. At this time, the roller pump timing mechanism is activated by moving on/off switch 214 to the on position. Now, the roller advances intermittently, injecting controlled doses of medication into the patient, over a medication delivery period which may be within the range of about several hours to forty-eight hours depending on factors such as the type of insulin being used and the dosage required by the patient. As the roller pump advances, the medication ahead of the roller is expelled from flexible reservoir tube 34 through second cannula 105, into flexible conduit 101, through first cannula 104 into the patient. It should be noted that second cannula 105 prevents medication from entering interior portion 67 of the purge chamber. The interior of the flexible reservoir tube behind the roller, which no longer contains medication, is filled with air entering through air-permeable, liquid-impermeable element 35. If the first end of the flexible reservoir tube were sealed, rather than containing element 35, there would be a tendency for the portion of the flexible reservoir tube which no longer contains medication to expand and create a negative pressure in the reservoir tube located behind the advancing roller thus requiring more power to advance the roller. This tendency is eliminated by the presence of element 35. At the end of the medication delivery period, the roller pump timing mechanism is deactivated by moving on/off switch 214 to the off position. Then the injection catheter is disconnected from the reservoir cassette, while first cannula 104 remains subcutaneously attached to the patient. Roller driving arm 202 is now rotated counter-clockwise to load position 206 and the reservoir cassette is removed from the roller pump and discarded. A new disposable reservoir cassette 30, filled with medication, is attached to the roller pump. Since the reusable injection catheter is filled with medication, with the first cannula in the patient, it is not necessary to supply an initial amount of medication into the catheter. It should be noted that resilient sleeve 110 prevents medication contained within the catheter from exiting through the second cannula when the injection catheter is not attached to the reservoir cassette. Before attaching the injection catheter to the reservoir cassette, the roller is again advanced to the start position. The medication, displaced by this roller motion, which is not needed to fill an empty injection catheter, flows into interior portion 67 of the purge chamber as depicted in FIG. 29. Any gases which may be present within interior portion 67 are forced out of the purge chamber through filter 64. The injection catheter is now connected to the reservoir cassette and the roller pump timing mechanism activated to start another medication delivery period. At the end of this second medication delivery period, it is preferred that the initial catheter be discarded and a delivery period started with a new injection catheter and a new injection site, although this step is not necessary.

It is preferred that cassette housing 37 be made of plastic such as polystyrene, polypropylene and polyethylene. It is also desirable to make upper housing portion 39 of a transparent plastic such as polystyrene so that the patient can readily observe the condition and position of the disposable reservoir cassette and roller pump components that are under the upper housing portion. It is also desirable to make the entire housing of a transparent material so that the components therein can be readily observed.

Flexible reservoir tube 34 should be constructed of materials that are compatible with the medication being stored therein and also flexible enough so as not to require large amounts of roller pump energy to compress the tube. Thermoplastic materials such as polyvinylchloride and thermoplastic elastomers and natural rubber may be used. However, coextruded materials are preferred since the material comprising the inner portion of the tube may be selected for a low moisture vapor transmission rate and for compatibility with the medication while the material comprising the outer portion may be selected for softness and lower energy consumption when subject to compression. When insulin such as U-100 Regular is the medication being used, a composite dual material tube using polyvinylchloride and a polyolefin such as polyvinylidene chloride is preferred with the polyolefin being located at the inner portion of the reservoir tube and acting as a liner for contacting the insulin.

Plug 51 of air-permeable, liquid-impermeable element 35 may be made of plastic such as polyethylene or polypropylene. Air-permeable, liquid-impermeable membrane 56 can be made of non-woven polymeric fabrics selected from polytetrafluoroethylene, polyester, polyvinylchloride, polypropylene, polyethylene and the like, preferably ranging in thickness of from about 0.003 to 0.010 inches (0.08 to 0.25 mm). Such materials as just described are available from W. L. Gore and Associates, Inc. of Elkton, Md., and are sold as GORE-TEX membrane products. The preferred element is polytetrafluoroethylene with a thickness of approximately 0.008 inches (0.2 mm). Membrane 56 may be attached to plug 51 via the use of adhesive or heat sealing. The plug may also be made entirely of air-permeable, liquid-impermeable material such as microporous polypropylene manufactured by Glasrock Products Inc., Porex Division, Fiarburn, Ga. Air-permeable, liquid-impermeable filter 64 of purge chamber 36 and venting member 126 of the alternative embodiment of the reusable injection catheter may be made of the same material as membrane 56 discussed hereinabove.

Cylinder 57 and sealing member 60 of purge chamber 36 may be constructed of a wide variety of rigid or flexible materials with elastomeric materials such as rubber and thermoplatic elastomers being preferred. Cylinder 57 and sealing member 60 may be made in one piece or as separate components held together, for example, by adhesive. Pierceable septum 59 may be constructed of a wide variety of elastomeric materials with rubber and thermoplastic elastomers being preferred.

Flexible conduit 101 of the reusable injection catheter is preferably made of extruded polymeric tubing with polyolefins or polyvinyl chloride being preferred. The preferred material for first cannula 104 is stainless steel. Connector housing 107 may be made of a wide variety of rigid materials with thermoplastic materials much as polypropylene and poly ethylene being preferred. Second cannula 105 may be made of stainless steel or of thermoplastic materials such as polypropylene and polyethylene or it may be molded as an integral part of connector housing 107. Resilient sleeve 110 is preferably made of self-sealing elastomeric material such as rubber and thermoplastic elastomers. Hold-down member 114 is preferably made of a moisture vapor transmissive, water and bacteria barrier material. A wide variety of medical grade adhesive coatings are commercially available for achieving adhesive properties of the hold-down member. A preferred material for the hold-down member with the adhesive thereon is a skin patch system manufactured by the Minnesota Mining and Manufacturing Company under the name Tegaderm.

It is preferred that all elements of the disposable reservoir cassette and the reusable injection catheter which contact the liquid medication or the patient, subcutaneously, should be sterile. Accordingly, materials should also be selected for compatability with the sterilization process being used.

Thus, the present invention provides a disposable reservoir cassette which can be inserted into and removed from a roller pump without removal of the injection cannula from the injection site and thus allowing the use of the same injection catheter for consecutively used reservoirs. The disposable reservoir cassette which can be purchased by the user in a pre-filled condition or filled by the user with a simple inexpensive filling system. Since the reservoir cassette contains all of the medication to be delivered to the user, a separate attached reservoir is unnecessary. The present invention also provides a reusable injection catheter with a resilient sleeve or sealing means at one end thereof to prevent loss of medication while changing reservoir cassettes and a hold-down member at the other end thereof to secure the subcutaneously placed injection needle.

What is claimed is:

1. A disposable reservoir cassette for use in delivering liquid medication to a user comprising:
   an elongate flexible reservoir;
   an air-permeable, liquid-impermeable element at a first end of said reservoir;
   access means at a second end of said reservoir for removable connection and fluid communication with an injection catheter; and
   a rigid cassette housing containing said reservoir therein and including a substantially circular back-stop supporting said reservoir along the length of said reservoir, said housing including an opening to allow contact with said reservoir by externally applied force adapted to compress said reservoir against said back-stop and drive any fluid contained therein in the direction toward said access means, said housing including a transfer port and holding means for fixedly holding said reservoir adjacent to said back-stop so that said access means is adjacent to said port.

2. The reservoir cassette of claim 1 wherein said reservoir is a flexibe tube.

3. The reservoir cassette of claim 1 wherein said element is plug of material inserted in the first end of said reservoir.

4. The reservoir cassette of claim 1 wherein said element comprises:
   a plug with a passageway therethrough; and
   an air-permeable, liquid-impermeable membrane attached to one end of said plug over said passageway.

5. The reservoir cassette of claim 4 wherein said membrane has a maximum pore rating of about 0.5 microns and serves as a substantial barrier against the passage of particles about 0.5 micron and larger.

6. The reservoir cassette of claim 1 wherein said housing comprises an upper housing portion and a lower housing portion joined in a plane substantially parallel to the plane containing said backstop.

7. The reservoir cassette of claim 6 wherein one housing portion is made of transparent material.

8. The reservoir cassette of claim 1 wherein said access means includes a pierceable septum.

9. The reservoir cassette of claim 8 wherein said pierceable septum includes a normally closed slit therethrough to be pierced by a cannula and further adapted to close upon removal of the cannula.

10. The reservoir cassette of claim 8 further comprising purge chamber means associated with said second end of said reservoir for accepting and storing a portion of the fluid originally contained within said reservoir which remains in the cassette after the fluid is delivered to the patient.

11. The reservoir cassette reservoir of claim 10 wherein said purge chamber means comprises:
   a cylinder having a distal end, a proximal end and a side wall;
   a sealing member at the distal end of said cylinder containing a centrally located orifice, said cylinder and said sealing member interposed between said reservoir and said septum, said sealing member engaging the second end of said reservoir and said septum engaging the proximal end of said cylinder wherein said cylinder, said septum and said sealing member define a cavity for accepting and storing a portion of the fluid originally contained within said reservoir, said orifice being in the fluid path between said reservoir and said cavity; and
   air venting means communicating between said cavity and the exterior of said purge chamber means.

12. The reservoir cassette of claim 11 wherein said air venting means includes an air-permeable, liquid-impermeable filter positioed to allow gases passing through said air venting means to pass through said filter, said filter having a maximum pore rating of about 0.5 microns and serving as a substantial barrier against particles about 0.5 micron and larger.

13. The reservoir cassette of claim 2 wherein said tube has a circularly shaped cross section.

14. The reservoir cassette of claim 1 further including securement means for cooperating with the source of externally applied force to removably hold said housing in a fixed position relative to said externally applied force.

15. The reservoir cassette of claim 14 wherein said securement means comprises an outwardly extending rib on an exterior surface of said housing adapted to removably engage the source of externally applied force, said rib including a surface adapted to align said housing with the source of externally supplied force when said housing is engaged therewith, said rib further adapted to limit the relative motion between said housing and the source of externally applied force during engagement and disengagement to motion of said housing which is substantially perpendicular to the direction of the externally applied force.

16. The reservoir cassette of claim 1 wherein said reservoir is made of material selected from the group consisting of thermoplastic materials, thermoplastic elastomers and natural rubber.

17. The reservoir cassette of claim 16 wherein said thermoplastic material is polyvinyl chloride.

18. The reservoir cassette of claim 16 wherein said thermoplastic material is a composite of polyvinyl chloride and a polyolefin material, said polyolefin material being located at the inner portion of said reservoir and acting as a liner for contacting fluids which may be present in said reservoir.

19. The reservoir cassette of claim 2 wherein said tube is removable from said housing.

20. The reservoir cassette of claim 2 wherein said tube contains liquid for delivery to a user.

21. The reservoir cassette of claim 20 wherein said liquid is insulin.

22. A reservoir cassette comprising:
   a compressible reservoir;
   a gas-permeable, liquid-impermeable element at one end of said reservoir;
   access means at the other end of said reservoir for gaining entry thereinto; and
   housing means for holding said reservoir so that said access means is accessible for transferring fluid from said reservoir and for allowing contact with said reservoir by externally applied forces adapted to compress said reservoir against said housing means and drive any fluid contained therein in the direction toward said access means.

23. A disposable reservoir cassette for use with a roller pump mechanism in delivering liquid medication to a patient comprising:
   a flexible reservoir tube;
   an air-permeable, liquid-impermeable element at a first end of said tube;
   access means at a second end of said tube for removable connection and fluid communication with an injection catheter;
   a rigid cassette housing containing said tube therein and including an opening to accept a roller of the roller pump mechanism and including a rigid substantially circular back-stop supporting said tube along the length of said tube, said housing having a transfer port therein and means to fixedly hold said tube adjacent to said back-stop so that said second end of said tube is adjacent to said port; and
   securement means for cooperating with the roller pump to position and removably hold said housing so that said back-stop is located substantially adjacent to the path of the roller pump roller whereby rotation of the pump roller is adapted to compress said tube sufficiently to drive any fluid contained therein in the direction toward said second end of said tube.

24. The reservoir cassette of claim 23 wehrein said element comprises:
   a plug with a passageway therethrough; and
   an air-permeable, light-impermeable membrane attached to one end of said plug over said passageway.

25. The reservoir cassette of claim 24 wherein said membrane has a maximum pore rating of about 0.5 micron and serves as a substantial barrier against the passage of particles about 0.5 micron and larger.

26. A reservoir tube assembly for use in a reservoir cassette comprising:
   a flexible reservoir tube;
   an air-permeable, liquid-impermeable filter element at one end of said tube; and
   access means at the other end of said reservoir for gaining entry thereinto.

27. The reservoir tube assembly of claim 26 wherein said tube contains liquid for delivery to a user.

28. The reservoir tube assembly of claim 27 wherein said liquid is insulin.

* * * * *